United States Patent
Lubrano et al.

(10) Patent No.: US 10,113,994 B2
(45) Date of Patent: Oct. 30, 2018

(54) NON-INVASIVE METHOD FOR MEASUREMENT OF PHYSICAL PROPERTIES OF FREE FLOWING MATERIALS IN VESSELS

(71) Applicant: ULTIMO MEASUREMENT LLC, Scituate, RI (US)

(72) Inventors: Francis M. Lubrano, Scituate, RI (US); Alexander M. Raykhman, East Greenwich, RI (US); Eugene Naidis, Ashkelon (IL); Valeriy Kashin, Cranston, RI (US)

(73) Assignee: ULTIMO MEASUREMENT LLC, Scituate, RI (US)

( * ) Notice: Subject to any disclaimer, the term of this patent is extended or adjusted under 35 U.S.C. 154(b) by 79 days.

(21) Appl. No.: 14/765,995

(22) PCT Filed: Feb. 6, 2014

(86) PCT No.: PCT/US2014/015174
§ 371 (c)(1),
(2) Date: Aug. 5, 2015

(87) PCT Pub. No.: WO2014/124182
PCT Pub. Date: Aug. 14, 2014

(65) Prior Publication Data
US 2016/0025687 A1    Jan. 28, 2016

Related U.S. Application Data

(60) Provisional application No. 61/761,543, filed on Feb. 6, 2013.

(51) Int. Cl.
*G01N 29/46* (2006.01)
*G01N 9/00* (2006.01)
(Continued)

(52) U.S. Cl.
CPC ............. *G01N 29/46* (2013.01); *G01F 1/86* (2013.01); *G01H 1/00* (2013.01); *G01N 9/002* (2013.01);
(Continued)

(58) Field of Classification Search
CPC ......... G01N 29/02; G01N 29/46; G01N 29/00
See application file for complete search history.

(56) References Cited

U.S. PATENT DOCUMENTS 4,117,716 A    10/1978 Simon
4,182,177 A    1/1980 Prough
(Continued)

FOREIGN PATENT DOCUMENTS

CN    1107231 A    8/1995
CN    1930454 A    3/2007
(Continued)

OTHER PUBLICATIONS

Engineering Toolbox, Nov. 10, 2006, Wayback Machine Snapshot.*
(Continued)

*Primary Examiner* — Manish S Shah
*Assistant Examiner* — Timothy Graves
(74) *Attorney, Agent, or Firm* — Lando & Anastasi, LLP

(57) ABSTRACT

Methods and apparatus for measuring physical properties of material in a vessel are provided. In one example, the method includes capturing a response to a vibration initiated by a source in mechanical communication with the vessel, generating a vibration response spectrum based on the response, and calculating at least one value of at least one physical property of the material based on at least one pre-established relationship between the at least one physical property and one or more characteristics of the vibration response spectrum.

10 Claims, 15 Drawing Sheets

(51) Int. Cl.
*G01N 11/16* (2006.01)
*G01H 1/00* (2006.01)
*G01N 11/00* (2006.01)
*G01N 29/02* (2006.01)
*G01N 29/34* (2006.01)
*G01N 9/24* (2006.01)
*G01N 9/32* (2006.01)
*G01F 1/86* (2006.01)

(52) U.S. Cl.
CPC ............... *G01N 9/24* (2013.01); *G01N 9/32* (2013.01); *G01N 11/00* (2013.01); *G01N 11/16* (2013.01); *G01N 29/02* (2013.01); *G01N 29/343* (2013.01); *G01N 2009/006* (2013.01); *G01N 2291/02818* (2013.01); *G01N 2291/02836* (2013.01); *G01N 2291/02881* (2013.01)

(56) References Cited

U.S. PATENT DOCUMENTS

| | | | |
|---|---|---|---|
| 4,292,522 A | 9/1981 | Okumoto | |
| 4,506,541 A | 3/1985 | Cunningham | |
| 4,574,328 A | 3/1986 | Maier | |
| 4,896,536 A | 1/1990 | Benz | |
| 4,954,997 A | 9/1990 | Dieulesaint et al. | |
| 5,015,995 A | 5/1991 | Holroyd | |
| 5,110,208 A | 5/1992 | Sreepada et al. | |
| 5,207,098 A | 5/1993 | Koch et al. | |
| 5,261,274 A | 11/1993 | Nemirow | |
| 5,359,541 A | 10/1994 | Pope et al. | |
| 5,515,733 A * | 5/1996 | Lynnworth | G01F 1/662 73/644 |
| 5,531,639 A | 7/1996 | Catalfamo | |
| 5,610,611 A | 3/1997 | McEwan | |
| 5,631,633 A | 5/1997 | Dreyer et al. | |
| 5,686,661 A | 11/1997 | Singh et al. | |
| 5,699,151 A | 12/1997 | Akasu | |
| 5,755,136 A | 5/1998 | Getman et al. | |
| 5,793,704 A | 8/1998 | Freger | |
| 5,807,092 A | 9/1998 | Mifune et al. | |
| 5,822,275 A | 10/1998 | Michalski | |
| 5,831,178 A * | 11/1998 | Yoshimura | G01F 1/8418 73/861.356 |
| 5,862,431 A | 1/1999 | Christensen | |
| 5,877,997 A | 3/1999 | Fell | |
| 5,892,576 A | 4/1999 | Gaechter | |
| 6,040,898 A | 3/2000 | Mrosik et al. | |
| 6,105,425 A | 8/2000 | Kawakatsu | |
| 6,111,211 A | 8/2000 | Dziedzic et al. | |
| 6,122,602 A | 9/2000 | Michalski et al. | |
| 6,128,982 A | 10/2000 | Gwin, Sr. | |
| 6,166,995 A | 12/2000 | Hoenes | |
| 6,192,751 B1 | 2/2001 | Stein et al. | |
| 6,194,215 B1 | 2/2001 | Rauh et al. | |
| 6,216,059 B1 | 4/2001 | Ierymenko | |
| 6,448,782 B1 | 9/2002 | Pakonen et al. | |
| 6,452,467 B1 | 9/2002 | McEwan | |
| 6,472,887 B1 | 10/2002 | Tullis et al. | |
| 6,481,276 B1 | 11/2002 | Neuhaus et al. | |
| 6,539,794 B1 | 4/2003 | Otto et al. | |
| 6,631,639 B1 | 10/2003 | Dam et al. | |
| 6,738,044 B2 | 5/2004 | Holzrichter et al. | |
| 6,738,720 B2 | 5/2004 | Odom et al. | |
| 6,834,556 B2 | 12/2004 | Cain et al. | |
| 6,945,094 B2 | 9/2005 | Eggen et al. | |
| 7,059,171 B2 | 6/2006 | Gysling | |
| 7,059,176 B2 | 6/2006 | Sparks | |
| 7,103,500 B2 | 9/2006 | Freger et al. | |
| 7,162,922 B2 | 1/2007 | Freger et al. | |
| 7,216,536 B2 | 5/2007 | Young et al. | |
| 7,469,033 B2 | 12/2008 | Kulik et al. | |
| 7,481,106 B2 | 1/2009 | Raykhman et al. | |
| 7,614,305 B2 | 11/2009 | Yoshioka et al. | |
| 8,174,258 B2 | 5/2012 | Raykhman et al. | |
| 2003/0079553 A1 | 5/2003 | Cain et al. | |
| 2003/0089161 A1 | 5/2003 | Gysling | |
| 2003/0230150 A1 | 12/2003 | Drahm et al. | |
| 2004/0060345 A1 | 4/2004 | Eggen et al. | |
| 2004/0173021 A1 | 9/2004 | Lizon et al. | |
| 2004/0181359 A1 | 9/2004 | Freger et al. | |
| 2005/0178198 A1 | 8/2005 | Freger et al. | |
| 2005/0224279 A1 | 10/2005 | Gilmer et al. | |
| 2007/0062260 A1 * | 3/2007 | Wenger | G01F 1/8409 73/54.01 |
| 2007/0068248 A1 | 3/2007 | Freger et al. | |
| 2008/0257036 A1 | 10/2008 | Chaudoreille et al. | |
| 2008/0307888 A1 | 12/2008 | Yoshioka et al. | |
| 2009/0084178 A1 * | 4/2009 | Sinha | G01N 9/002 73/32 A |
| 2010/0011882 A1 | 1/2010 | Gebhardt et al. | |
| 2012/0222471 A1 | 9/2012 | Raykhman et al. | |

FOREIGN PATENT DOCUMENTS

| | | | |
|---|---|---|---|
| CN | 100445703 C | 12/2008 | |
| CN | 101809420 A | 8/2010 | |
| EP | 1601936 A2 | 12/2005 | |
| EP | 1709149 A2 | 10/2006 | |
| JP | 01-311250 A | 12/1989 | |
| JP | H11248514 A | 9/1999 | |
| RU | 2194977 C2 | 12/2002 | |
| WO | 2004074782 A2 | 9/2004 | |
| WO | 2005062945 A2 | 7/2005 | |
| WO | 2006104485 A1 | 10/2006 | |
| WO | 2009118542 A1 | 10/2009 | |
| WO | WO 2011017355 | * 2/2011 | G01N 9/00 |

OTHER PUBLICATIONS

A Paradigm Here is Provided by the Famous Burgers Equation [ Dave Harris proposal at www.maths.manchester.ac.uk/~dh/MScProjects/NumAnalProj07.html, en.wikipedia.org/wiki/Burger%27_equation ].
Webpages for "VBS Series" from www.stiautomaticproducts.com.
Webpages from www.astronet.ru including excerpt from on-line article "Earth's Crust Resesarch: Geophysical Methods" and concise explanation of relevance in English.
Webpages from www.hitech.com including excerpt of on-line article "Penetrating Pulse Technology".
Webpages with "VisselCheck ST" marketing materials, from www.canongatechnology.co.uk.
Cover and excerpt from the Theory of Sound by John William Strutt, Baron Rayleigh, vol. I, Second Edition, Dover Publications, pp. 180, 181, 246, 247.
Cover, and excerpt from Marks' Standard Handbook for Mechanical Engineers, 10th Edition, by Eugene A. Avallone and Theodore Baumeister III, McGraw-Hill,pp. 12-117.
Cover, Forward, and excerpts from B. M. Yavorsky and A.A. Detlaf, Physics Handbook, 3.sup.rd edition, M. Nauka, 1990 and concise explanation of relevance in English.
Search Report from corresponding Chinese Application No. 201080041950.9 dated Mar. 28, 2013.
Sontag, Eduardo D., "Mathematical Control Theory: Deterministic Finite Dimensional Systems", Second Edition, Texts in Applied Mathematics/6, 1998.
Viscosity: http://hypertextbook.com/physics/matter/viscosity/.
International Search Report from corresponding PCT/US2014/015174 dated Nov. 17, 2014.

* cited by examiner

NON-INVASIVE METHOD FOR
MEASUREMENT OF PHYSICAL
PROPERTIES OF FREE FLOWING
MATERIALS IN VESSELS

CROSS-REFERENCE TO RELATED
APPLICATIONS

This application is a U.S. National Stage Application under 35 U.S.C. § 371 of International Application No. PCT/US2014/015174, filed Feb. 6, 2014, which claims priority under 35 U.S.C. § 119(e) to U.S. Provisional Application 61/761,543, titled "NON-INVASIVE METHOD FOR MEASUREMENT OF PHYSICAL PROPERTIES OF FREE FLOWING MATERIALS IN VESSELS," filed on Feb. 6, 2013, both of which are hereby incorporated herein by reference in their entirety.

BACKGROUND

Technical Field

Aspects disclosed herein relate to systems and methods for non-invasive measurement of physical properties of non-gaseous, free flowing matter in a vessel, and more particularly, determining the density, viscosity, volumetric flow, and shear resistance relating variables of the non-gaseous, free flowing matter.

Discussion

PCT Application No. PCT/US10/44292, titled METHOD AND APPARATUS FOR MEASUREMENT OF PHYSICAL PROPERTIES OF FREE FLOWING MATERIALS IN VESSELS, filed Aug. 3, 2010, which is hereby incorporated herein by reference in its entirety, describes a percussion method of measuring physical properties of non-gaseous materials within vessels. Some examples disclosed within PCT Application No. PCT/US10/44292 solve equations in real time. These equations include at least two variables that should be correctly identified as estimating variables. Further, these equations belong to the class of equations describing free flowing material motion in a most general way, much like Navier-Stokes and Burger's equations. Solving these equations numerically requires powerful computing apparatus, occupies substantial run time, and is based on special computing techniques (e.g., Globally convergent Broyden algorithm, Newton-Krylov algorithm, trust-region dogleg algorithm, Nonlinear Least Squares Levenberg-Marquardt method, Nonlinear Least Squares Gauss-Newton method) that could be unstable once applied to functions with a noticeable random component.

SUMMARY

The focus of the present disclosure is the further improvement of the Ultimo-branded Percussion Technology, which applications include level, density, viscosity measurement and mass flow measurement. In some examples, mass flow measurement is enabled when the Percussion technology is combined with volumetric flow measuring technology. In other examples, a new method for non-invasively measuring physical properties of the free flowing material in a vessel is described. The method does not require solving any estimating variables-based equations in real-time or near real-time and does not include the steps of the material sample preparation and measurement for the purpose of calibrating the measurement instrument.

Aspects and examples disclosed herein manifest an appreciation that measurement of content material's physical variables (e.g., density, viscosity of heterogeneous liquids, amount of entrained air in the vessel content, level deviations, etc.), when performed quickly and without device calibration, presents an opportunity for broad applicability, improved accuracy and greater stability for the percussion method for measurement of physical properties of non-gaseous materials.

According to one example, a method for non-invasive measurement of physical properties of a non-gaseous free flowing matter filling a vessel to a known level or to a constant level is provided. The method includes acts of initializing vibration at least at a single predetermined position on the outside wall of the vessel filled to a predetermined level with non-gaseous free flowing matter, capturing the wall oscillatory response to the mechanical load, analyzing the captured response, generating the vibration response spectrum and producing readings of values of at least one physical property of the free flowing matter. In one example, the measurement is based on the pre-established relationship or relationships between the measured property or properties and at least one property of the vibration spectrum. Each pre-established relationship may be defined by the vessel's configuration and type of the vessel's attachment to an immobile plane with mass considered to be substantially greater than the overall mass of the vessel.

The method allows for the measurement of at least the density of homogeneous liquids, bulk density of heterogeneous liquids like emulsion, pulp, slurry and loose solid materials.

Examples of vessels used in conjunction with the method include silos, tanks, and pipes, among others. In the method, the filling material may be a homogeneous liquid, a heterogeneous liquid, or a loose solid material. In the method, the filling material could be still or it could be moving through the vessel. Additionally, in the method, the vibration may originate through a mechanical temporal load applied to the outside wall of the vessel; the load being actuated by a variety of mechanisms, including one or more of a solid material body interaction (also called a solid body interaction) with the wall, a fluid-dynamic interaction including air and a liquid agent, a ballistic percussion interaction and an electro-dynamic interaction.

In the method, the mechanical load may include a single pulse, a trainload of pulses (also called a pulse train), a periodic pulse, and a continuous periodical load (also called a continuous periodical pulse). Additionally, in the method, the mechanical load may be modulated as one of an amplitude modulation, a frequency modulation, a pulse modulation, a pulse-code modulation, a pulse-width modulation and a combination thereof, and the mechanical load may be originated by the transformation of a source of driving energy selected from one of an electromagnetic drive, a mechanical energy used in springs, a pneumatic apparatus, a hydraulic apparatus and a ballistic percussive apparatus. The source of driving energy may dictate the type of actuating mechanism discussed above. For example, a ballistic percussive apparatus causes a ballistic percussion interaction between the temporal load applied to the outside wall of the vessel and the filling material.

In the method, the act of capturing may include an act of converting the oscillation into a signal, such as a digital signal, acquirable by a signal processing mechanism and further analyzable by a data processing mechanism resulting in creating a set of informative variables serving as an input for generating evaluating variables of the method. In the method, an outcome of the captured signal analysis includes, but is not limited to, at least one of the following sets of the informative variables characterizing the strength of the wall response to the strike (i.e., variables characterizing a magnitude of an oscillation initiated by the strike): a) set of maximums of the filtered and rectified signal obtained on a moving time-window greater then a sampling period; b) sum of the maximums; c) sum of differences between the adjacent maximums. Further, in the method, the outcome of the captured signal analysis may include a set of maximums of obtained on a time-window greater than a sampling period. In addition, in the method, the outcome of the captured signal analysis may be the wall response time calculated under the condition that the captured signal is greater than a set threshold. Moreover, in the method, the outcome of the captured signal analysis may be the signal logarithmic decrement or damping factor. Additionally, in the method, the outcome of the captured signal analysis may be the signal harmonic spectrum.

According to another example, a method for non-invasive measurement of physical properties of a non-gaseous free flowing matter moving through the fully filled vessel is provided. The method comprises the acts of: initializing vibration at least at a single predetermined position on the outside wall of the vessel; capturing the wall oscillatory response to the mechanical load; analyzing the captured response; generating the vibration response spectrum and producing readings of values of at least one physical property of the free flowing matter. In one example, the measurement is based on the pre-established relationship or relationships between the measured property or properties and at least one property of the vibration spectrum. Each pre-established relationship may be defined by the vessel's configuration and type of the vessel's attachment to an immobile plane which mass is considered to be substantially greater than the overall mass of the vessel. In one example of the method, the property of the vibration spectrum is selected to be the frequency of the spectrum fundamental harmonic in order to enhance the method's invariance to changes of the environment including ambient temperature variation and changes in the material flow rate.

In one example of the method directed to pipes, the measured density of the free flowing matter is the bulk density defined by the volume occupied by the matter between the pipes' supporting members. In this example, the pre-established relationship or relationships between the measured property or properties and at least one property of the vibration spectrum is represented by the following formula.

$$\rho_c = \frac{\beta^4 E I g}{\pi^3 L^4 d^2 f^2} - \frac{4cgM_s}{\pi L d^2} - \frac{\rho(D^2 - d^2)}{d^2}$$

$$I = q(D^4 - d^4)$$

$$M_s = \frac{1}{g} W_s$$

Where D—Pipe OD;
d—Pipe ID;
ρ—Density of the pipe wall material
E—Young Modulus of the pipe wall material
I—Moment of Inertia of the pipe cross sectional area
g—Gravity constant
$W_s$—Weight of the vibration sensor used for producing the vibration spectrum
$M_s$—Mass of the vibration sensor
B, c—Measurement application-dependent parameters
q—Measurement units conversion factor According to another example, a method for non-invasive measurement of physical properties of a non-gaseous free flowing matter is provided. The method comprises the acts of capturing the wall oscillatory response to a mechanical disturbance produced by an external source, e.g. a working pump or a compactor, etc. or internally by the friction of the moving matter against the internal surface of the pipe; analyzing the captured response; generating the vibration response spectrum and producing readings of values of at least one physical property of the free flowing matter. In one example, the measurement is based on the pre-established relationship or relationships between the measured property or properties and at least one property of the vibration spectrum. Each pre-established relationship may be defined by the vessel's configuration and the type of the vessel's attachment to an immobile plane which mass is considered to be substantially greater than the overall mass of the vessel.

In one example of the method, the act of capturing the vibration response is supported by an automatic adjustment of the gain of the vibration capturing mechanism thereby providing for the stability and accuracy of the outcome of the consequent act of generating the vibration spectrum.

In an example directed to measuring the density of the free flowing matter, the monitoring of the fundamental harmonic of the vibration spectrum is based on the a priori knowledge of the content material's expected measurement range. A search zone within the vibration response spectrum may be defined by calculating values of the fundamental harmonic frequency that are linked to upper and lower boundary values of the measured density within the known density range and with the consequent broadening of the calculated frequency range to account for possible discrepancies between the theoretical parameters of the single degree of freedom mechanical model and the parameters of the actual measurement application, e.g., pipe stiffness.

In another example, to further enhance the long term stability of the measurement method, the method includes computation of a correction to the measured variable values to account for noise caused due the susceptibility to thermal energy of electronic parts of a vibration sensor. In this example, the correction is computed as a function of a link between the temperature inside the vibration sensor and the measured variable. In another example, the method includes computation of another correction to the measured variable values to account for noise caused due the susceptibility to thermal energy of mechanical parts of the vibration sensor. In this example, the correction is computed as a function of a link between the ambient temperature and the measured variable. The utilization of the links depends on the environmental conditions such that each of the links could be used solely and independently or both links could be used simultaneously and in some interrelationship.

In another example of the method, the ambient temperature data obtained within a predefined proximity of the vessel's outer surface could be used for implementing the process temperature compensation function when certain properties should be measured at a set process temperature regardless of the temperature value existing on the moment of measurement. When executed, this temperature compensation function converts a value of a physical property measured at a recorded temperature to a value that the physical property would be measured to have at the set process temperature. The converted value may be referred to as a compensated value. This function is important in various chemical engineering measurement applications.

According to another example, a percussion-based device for non-invasively measuring density, viscosity, level deviation and presence of a free-flowing non-gaseous material contained in a vessel is provided. In some embodiments, portions of the device's moving parts are dynamically isolated from the oscillating vessel wall, thereby allowing undisturbed monitoring of combined oscillation of the vessel wall and a portion of the contained material attached to the wall. Using this approach, these embodiments have enhanced sensitivity, accuracy and precision of measurement over conventional measurement devices.

According to one example, a device for non-invasively measuring physical properties or physical variables of the material contained in a vessel is provided. A non-limiting list of examples of the physical properties the device can measure include: density, viscosity, level deviation, presence of a free-flowing non-gaseous material and mass flow rate. The device includes a housing, a coupler, a striker, a driver, a controller, a sensor, a signal acquirer, a processor, an analyzer, an interface, and a stabilizer. The coupler couples the housing to a vessel wall. The driver causes the striker to move toward the vessel wall. The controller controls the motion of the striker. The sensor senses the combined oscillation of the vessel wall and the material contained in the vessel after the oscillation is initiated by the striker coming in dynamic contact with the vessel wall. The signal acquirer acquires an oscillatory signal representative of the oscillation and conditions the signal for further processing. The processor produces the measured content material physical variables-related data by processing said signal. The analyzer processes the produced data to determine the measured physical variables. The interface provides the measured variables to external entities. The stabilizer provides long term measurement stability to the device.

In some examples, the coupler of the device is connected to a thin membrane situated on the opening in the vessel wall, thereby providing for improved sensitivity, accuracy and precision of measurement. In this example, the thin membrane may be disposed between the vessel and the coupler. In other examples, where the vessel is a pipe, tube or conduit, the coupler is connected to a thin-walled member of the same construction as the vessel that is surrounded by the vessel, thereby providing for improved sensitivity, accuracy and precision of measurement.

According to another example illustrated in FIG. 10, a reaction force is directed toward the pipe wall. The reaction force is caused by the inertia force of the moving and then quickly ceasing to move striker. The reaction force is used to initiate oscillation in the vessel body without the striker coming in dynamic contact with the vessel wall.

In another example illustrated in FIGS. 11 and 12, the vessel body is forced to oscillate by a vibrating member of the vessel's construction such as a motor, a pump, a compactor or a local resistance inside the vessel that causes eddy currents within the material. In this example, the device's sensor acquires the vibration of the vessel body despite the device's striker being immobile.

In an application of the device directed to measuring the mass flow rate of the material moving through a pipe, the device is equipped with a volumetric flow measuring unit that measures the mass flow of the pipe content by multiplying the measured material density by the measured volumetric flow. In an example having a vortex-type volumetric flow, the device has an immobile (or removed) striker. This device utilizes pipe body vibration initiated by a source located outside of the device. In particularly, the vibration is initiated by the turbulence generated when the material flow meets resistance from the vortex flow meter shedder member as shown in the functional diagram of FIG. 13.

According to at least one embodiment, a method for measuring physical properties of material in a vessel is provided. The method includes acts of initiating a vibration on a wall of the vessel, capturing a response to the vibration, generating a vibration response spectrum based on the response and producing a reading of a value of at least one physical property based on at least one pre-established relationship between the physical property and one or more characteristics of the vibration response spectrum.

The method may further include an act of computing the at least one pre-established relationship based on the type and the placement of the vessel's supports. In the method, the act of producing a reading may include producing a reading of a material bulk density value or a material viscosity value.

According to another embodiment, a device for measuring physical properties of material in a vessel is provided. The device includes a striker configured to initiate a vibration on a wall of the vessel, a sensor configured to capture a response to the vibration, and an isolator configured to prevent noise caused by motion of the apparatus or within the apparatus.

According to one example, method for measuring physical properties of material in a vessel is provided. The method includes acts of capturing a response to a vibration initiated by a source in mechanical communication with the vessel, generating a vibration response spectrum based on the response, and calculating at least one value of at least one physical property of the material based on at least one pre-established relationship between the at least one physical property and one or more characteristics of the vibration response spectrum.

In one example, the method further includes initiating the vibration on a wall of the vessel. In a further example, initiating the vibration includes at least one of initiating a solid body interaction with the wall, initiating a fluid-dynamic interaction with the wall, initiating a ballistic percussion interaction with the wall, and initiating an electro-dynamic interaction with the wall.

In another example, initiating the vibration includes applying a mechanical load to the outside wall of the vessel. According to a further example, the mechanical load includes at least one of a single pulse, a pulse train, and a periodic pulse. In at least one example, the mechanical load is modulated according to at least one of amplitude modulation, frequency modulation, pulse modulation, pulse-code modulation, and pulse-width modulation.

In some examples, capturing the response includes: converting an oscillation into a digital signal; and analyzing the digital signal to calculate at least one of a wall response time, a damping factor, a signal harmonic spectrum, and a variable characterizing a magnitude of the oscillation. In a further example, capturing the response includes adjusting a gain applied to the response.

According to at least one example, the method further includes determining the pre-established relationship based on a configuration of the vessel and a type of attachment between the vessel and another object.

According to another example, the method further includes determining a search zone within the vibration response spectrum.

According to yet another example, the method further includes computing a correction to the at least one value.

In at least one example, the method further includes measuring an ambient temperature within a predefined proximity of the vessel, determining a difference between the ambient temperature and a process temperature, and converting the at least one value to a compensated value based on the difference.

In another example, calculating the at least one value includes calculating at least one value of at least one of material bulk density of the material and viscosity of the material. In a further example, calculating the at least one value includes calculating at least one value of at least one physical property of at least one of a homogeneous liquid, a heterogeneous liquid, and a loose solid. According to another example, calculating the at least one value includes calculating at least one value of at least one physical property of at least one of a moving material and a still material. According to another example, calculating the at least one value includes calculating at least one value of at least one physical property of the material based on at least one pre-established relationship between the at least one physical property and a frequency of a spectrum fundamental harmonic.

In one example, capturing the response includes capturing a response to a vibration initiated by a source in mechanical communication with at least one of a silo, a tank, and a pipe. According to another example, capturing the response includes capturing a response to a vibration initiated by at least one of an external source and an internal source.

According to one example, an apparatus for measuring physical properties of material in a vessel is provided. The apparatus includes a housing. The housing includes: a striker configured to initiate a vibration on a wall of the vessel, a sensor configured to capture a response to the vibration, an isolator configured to prevent noise caused by motion of the apparatus or within the apparatus, and an analyzer configured to determine at least one value of at least one physical property of the material based on data generated from the response.

According to one example, the at least one physical property includes at least one of density, viscosity, level deviation, mass flow rate, and presence of a free-flowing non-gaseous material.

In another example, the apparatus further includes a coupler configured to couple the housing to the vessel. In at least one example, the housing further includes a driver coupled to the striker, the driver being configured to move the striker toward the vessel. According to another example, the driver is at least one of an electromagnetic driver, a spring driver, a pneumatic driver, a hydraulic driver, and a ballistic percussive driver.

In one example, the housing further includes a controller configured to control the driver. According to at least one example, the housing further includes a signal acquirer configured to: acquire an oscillatory signal representative of the response, and condition the oscillatory signal for further processing. In at least one example, the housing further includes a processor configured to process the oscillatory signal to provide the data to the analyzer. In another example, the housing further includes an interface configured to provide the at least one value to an external entity.

In at least one example, the apparatus further includes a thin membrane disposed between the vessel and the coupler.

In accordance with one example, an apparatus for measuring physical properties of material moving through a vessel is provided. The apparatus includes a housing. The housing includes: a sensor configured to capture a response to a vibration, an analyzer configured to determine volumetric flow and density of the material based on data generated from the response, and a volumetric flow measuring unit configured to calculate a mass flow rate of the material by multiplying the density by the volumetric flow.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any example or embodiment disclosed herein may be combined with any other example or embodiment. References to "an example," "some embodiments," "an alternate example," "various embodiments," "one example," "at least one embodiment," "this and other examples" or the like are not necessarily mutually exclusive and are intended to indicate that a particular feature, structure, or characteristic described in connection with the example or embodiment may be included in at least one example or embodiment. The appearances of such terms herein are not necessarily all referring to the same example or embodiment.

BRIEF DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of the examples disclosed herein. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. In the figures:

FIG. 3 is a graph of the family of curves representing the relationship between the material bulk density and the frequency value of the pipe's fundamental harmonic; the pipe is clamped at two sides; the distance between the clamps=50 in.; the pipe OD=3.5 in.; the pipe ID=3.07 in.;

DETAILED DESCRIPTION

Figure 1:
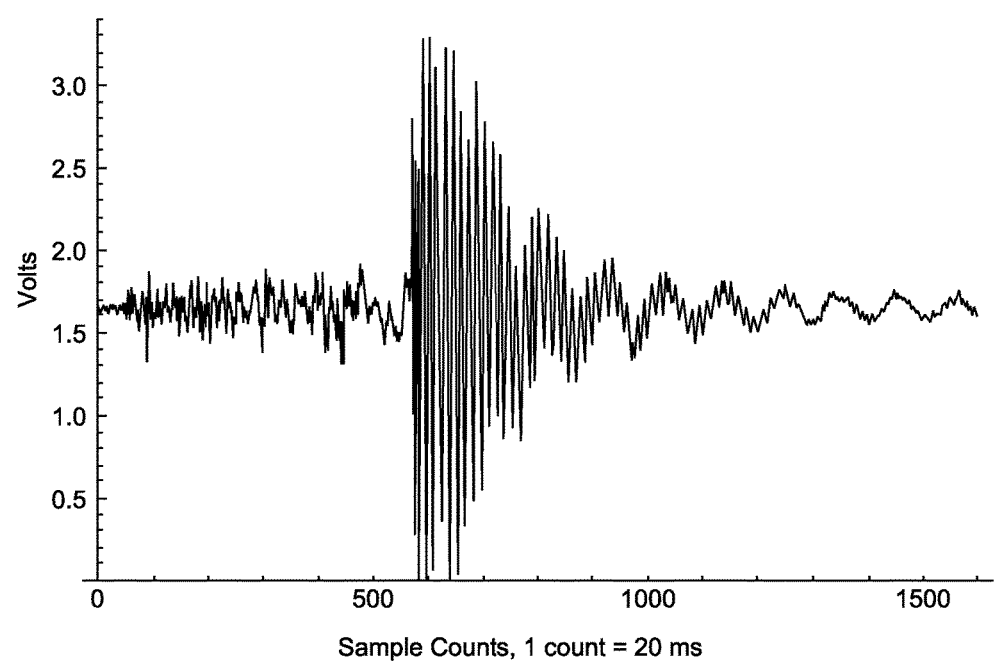
FIG. 1 is a time diagram of the pipe vibration response captured by a vibration sensor, such as the Ultimo DVM vibration sensor.
Figure 2:
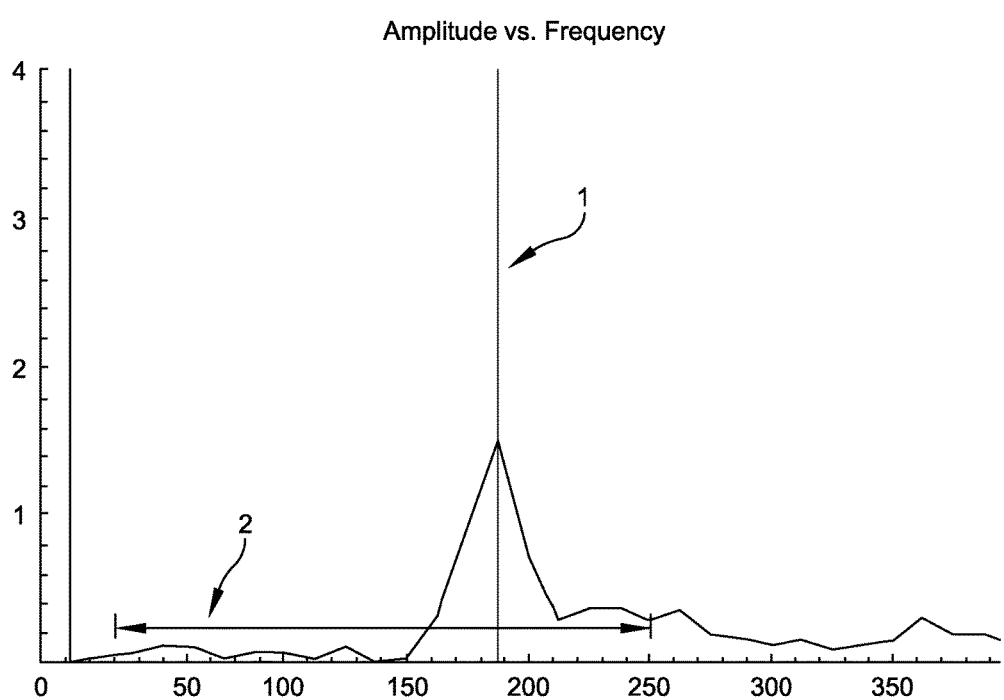
FIG. 2 is a plot of the vibration spectrum of the signal shown in the FIG. 1: 1—Spectrum line associated with the pipe's vibration fundamental harmonic; 2—Search zone on the frequency domain for the fundamental harmonic frequency tracking.
Figure 3:
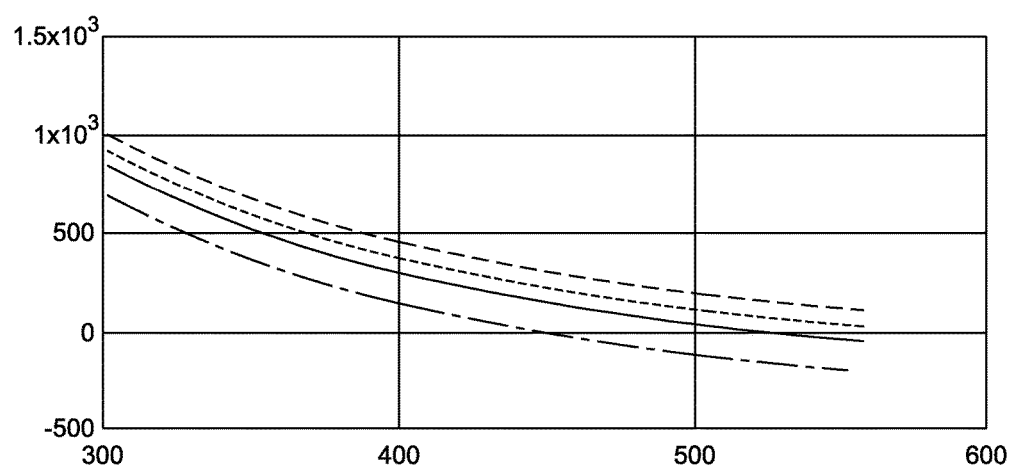

Aspects and examples disclosed herein relate to apparatus and processes for determining physical properties of a material housed within a vessel. For instance, according to one example, an apparatus includes a striker, vibration sensor and controller configured to determine the density belonging to a set of measured physical variables characterizing the vessel content. In some examples, the non-gaseous material is a fluid. In other examples, the non-gaseous material is a solid. According to another example, an apparatus, such as the apparatus described above, executes a method for determining physical properties of a material housed within a vessel. While executing the exemplary method, the apparatus determines the density of a non-gaseous material disposed within the vessel by calculating the instantaneous density values using a pre-established relationship between the density and the measured property or properties of the vibration spectrum of the vessel equipped with the vibration sensor.

It is to be appreciated that examples of the methods and apparatuses discussed herein are not limited in application to the details of construction and the arrangement of components set forth in the following description or illustrated in the accompanying drawings. The methods are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls. Moreover, titles or subtitles may be used in the specification for the convenience of a reader, which shall have no influence on the scope of the embodiments disclosed herein.

Measurement Apparatus

Some examples disclosed herein improve upon, operate with, or adapt to devices described in PCT Application No. PCT/US10/44292. According to one example, a device for non-invasively measuring physical properties of a free-flowing non-gaseous material contained in a vessel is provided. The device includes a driver that causes a striker to move toward, and physically impact, a wall of the vessel. The device is arranged to mechanically isolate (after a strike has been applied to the vessel wall) the device's mass and motion (and the mass and motion of the device's internal and external components) from the combined oscillation of the vessel wall and the material contained within the vessel. It is to be appreciated that such mechanical isolation does not include, however, any sensing or coupling components of the device. These components remain in mechanical communication with the vessel wall after the strike has been applied. The isolation will reduce (or eliminate) interference to the oscillation caused by the mass and motion of the device and its components.

Figure 6:
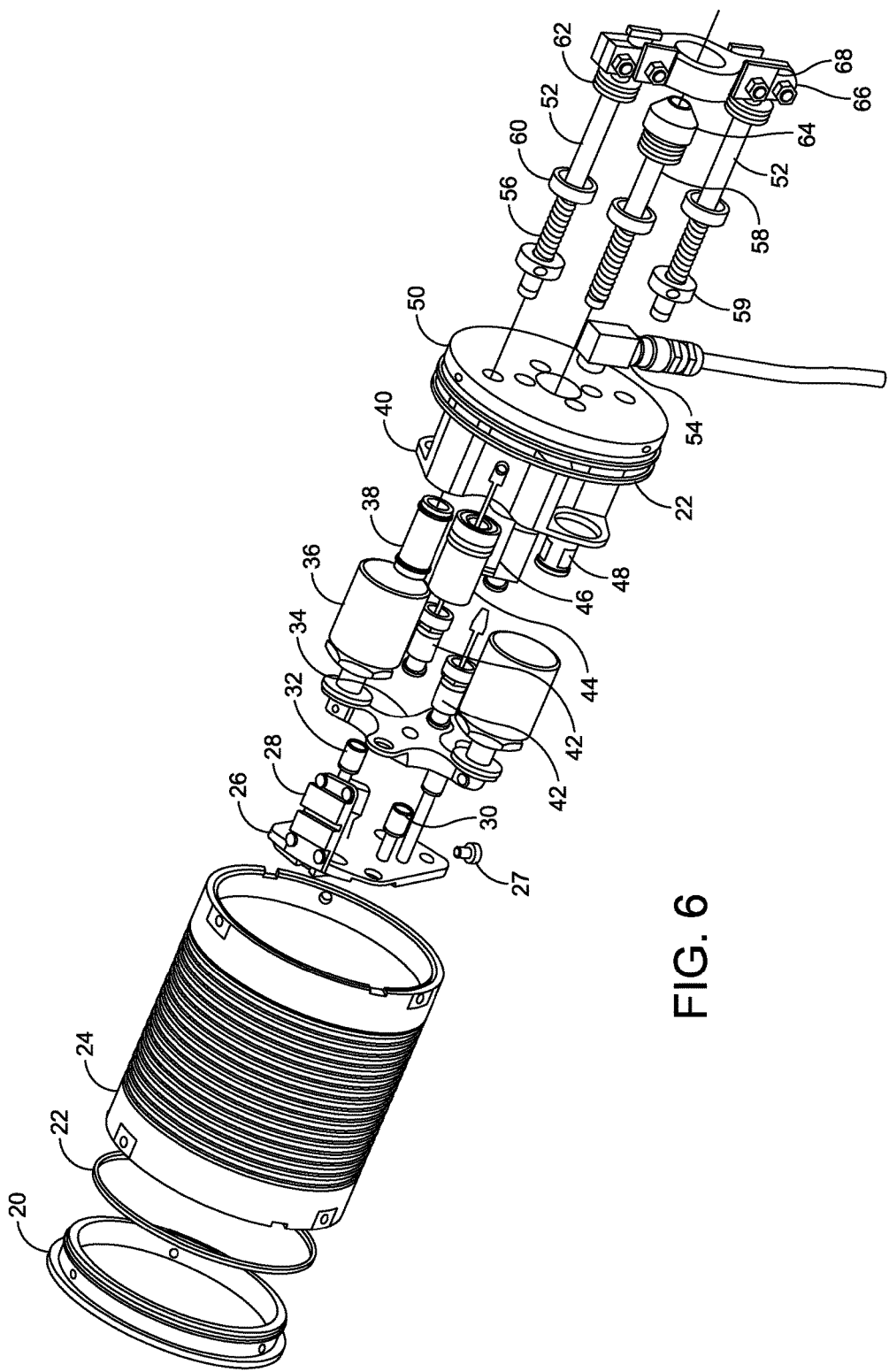
FIG. 6 depicts an exploded 3D view of the mechanical design of an embodiment.
Figure 7:
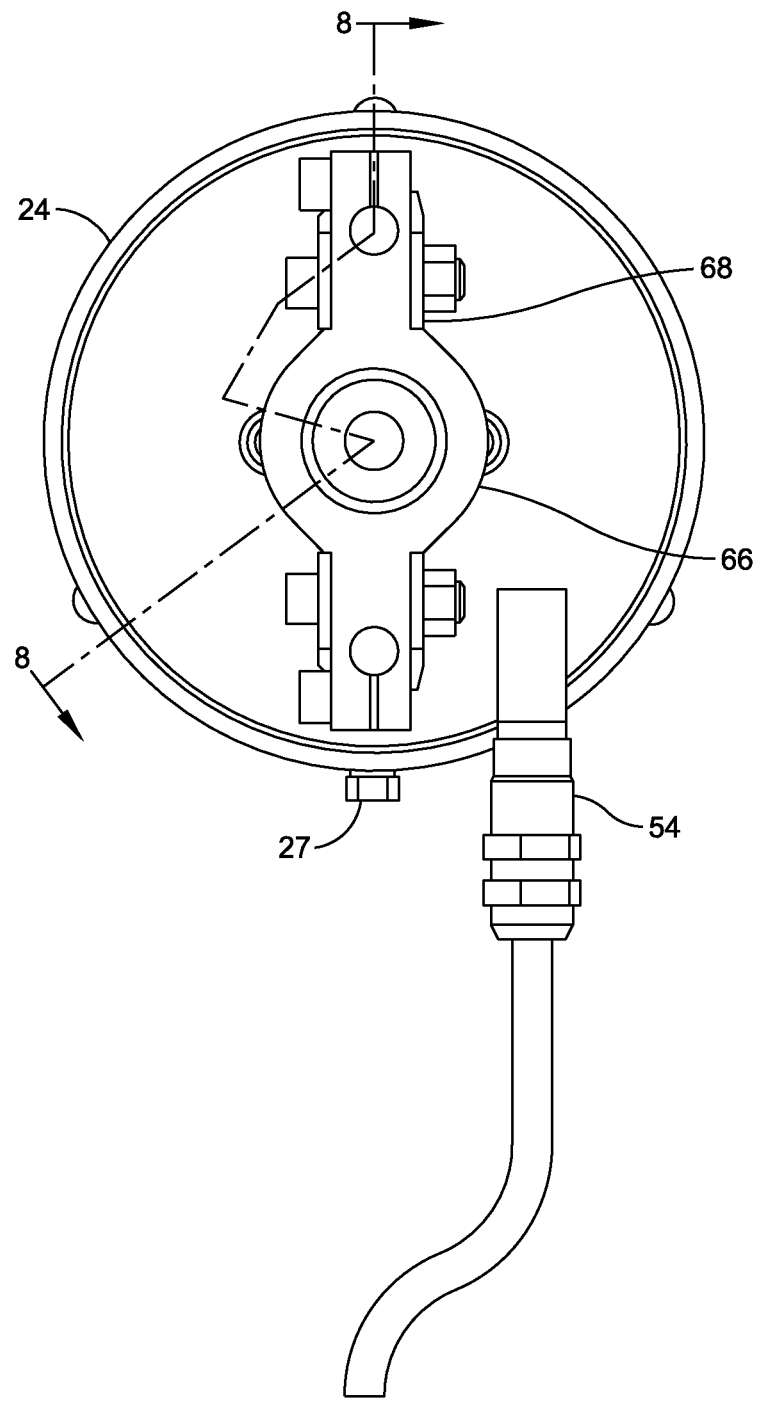
FIGS. 7, 8 are the assembly drawings of the mechanical design of an embodiment.
Figure 8:
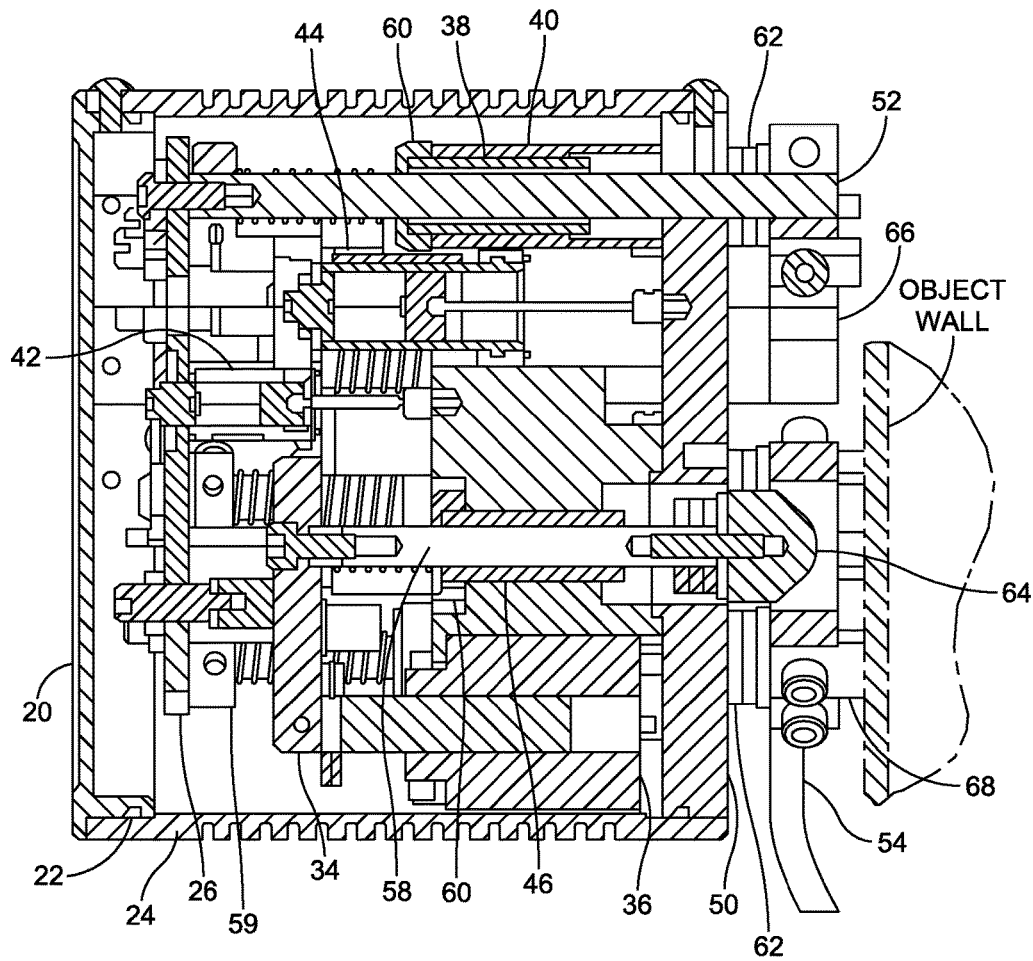
Figure 9:
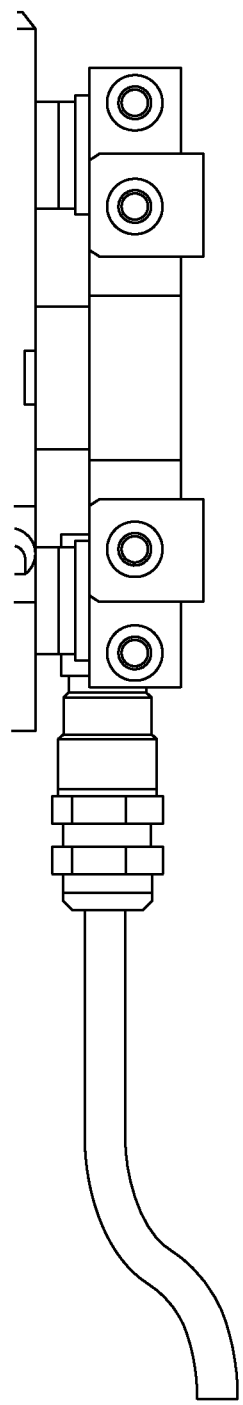
FIG. 9 illustrates a side view of an embodiment.

FIGS. 6-8 illustrate embodiments including components designed to mechanically isolate a device (other than its sensing and coupling components) from a vessel after the device applies a strike. The device includes a housing 40 mounted on a support plate 50, a body cover 24, and an end cover 20. The mounting plates 68 connect with an object (such as a vessel) wall and have holes for a mounting bracket 66. The mounting bracket 66, guide posts 52 and a top support plate 26 are connected by screws (or any other suitable fastener), and form a guide frame for the housing 40. The housing 40 and the support plate 50 have holes for linear bearings 38, 46, and 48 which allow slide movement of the housing 40 on the guide posts 52.

A striker linear bearing mounted in the center of the housing 40 serves as guide for a striker shaft 58. A first end of the shaft 58 has elastic striker tip 64, and a second end connected with a cross beam 34. The cross beam 34 is connected with cores of a pair of solenoids 36 and with pair of dashpots 44. Rods of the dashpots 44 are connected with the support plate 50. A pair of dashpots 42 is connected by a first end with the top support plate 26 and by a second end with the housing 40. A pair of bumpers 32 serves as a positive stop for the housing 40. A pair of bumpers 30 serves as a positive stop for the cross beam 34, which is connected to the solenoid cores and the striker shaft 58. The body cover 24 has a vent breather 27. A sensor 28 is rigidly connected with the stationary part of the illustrated embodiment. Seals 22 are mounted on the end cover 20 and the support plate 50. Return springs 56 are mounted on the posts 52 and the striker shaft 58. These springs are supported by spring support washers 60 and are adjusted by adjusting collars 59. Bumper washers 62 serve as stops for support plate 50. An electrical conduit 54 may further be attached or in communication with support plate 50.

At the moment of time when the driving voltage pulse energizes the solenoid of the driver, its core begins moving toward the vessel wall that accelerates the striker resulting in making an impact at the vessel wall. During the striker's motion toward the vessel wall, a reactive force of this motion creates a movement of members 40, 20, 24 and 50 in the direction opposite to the striker motion. In this process, Dampers 42, 44 are smoothing mutual oscillations of all moving members of the device. After each strike, recoil springs bring the moving members to their initial positions. A sensor (accelerometer in the one embodiment) that measures the wall oscillation is firmly linked to the vessel wall by posts 5, top support plate 26 and mounting bracket 66. Because immediately after the impact has been applied to the vessel wall, the movable masses of the striker 58 and the housing 40 become involved in a decaying oscillating process of relative motion by sliding over the guiding posts 52, their influence on the vessel wall oscillation is minimized, thereby allowing an undisturbed monitoring of combined oscillation of the vessel wall and the portion of the material attached to the wall inside the vessel.

Figure 10:
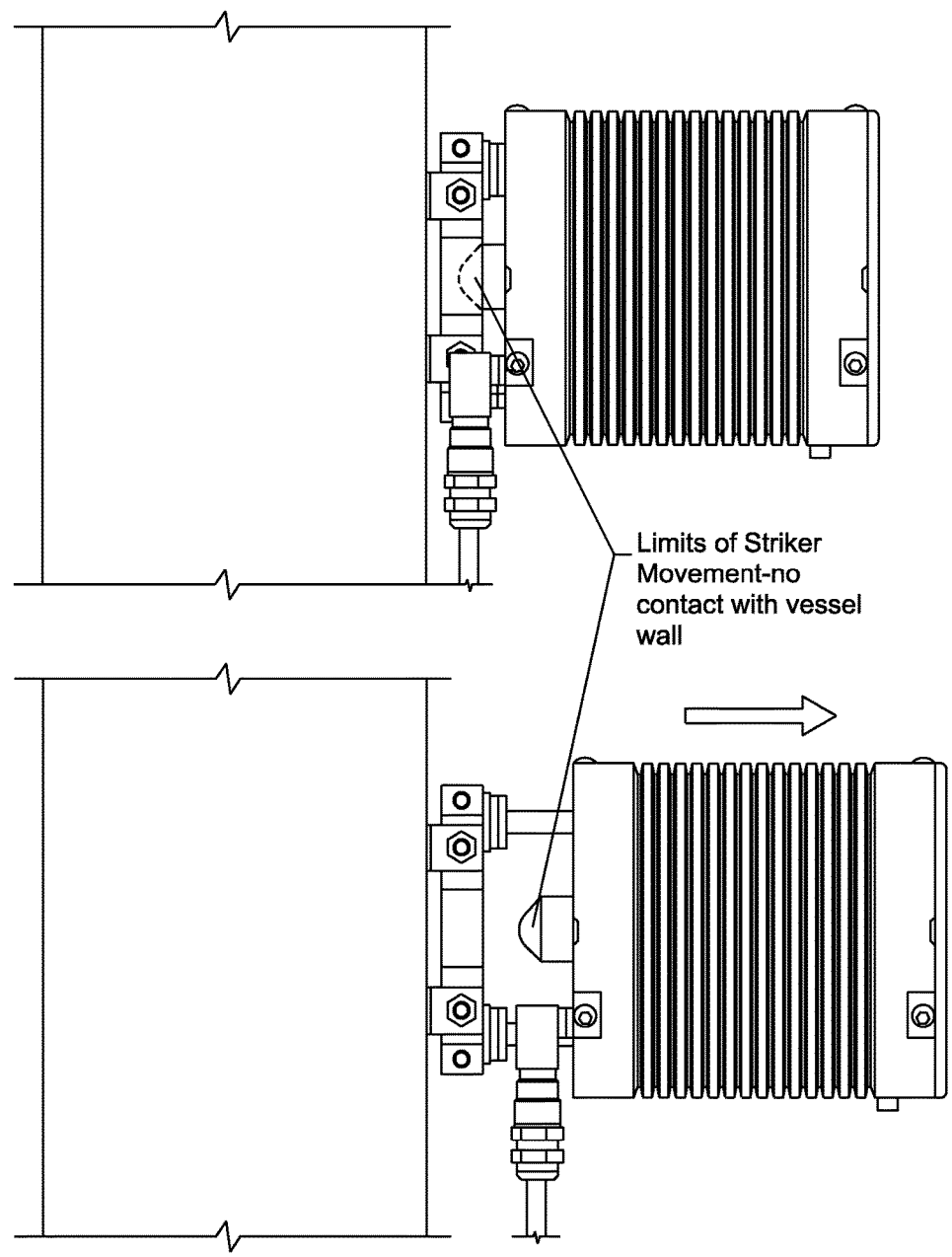
FIG. 10 illustrates an inertia force-based actuation of the vessel body in an embodiment.

According to another example illustrated in FIG. 10, a reaction force is directed toward the pipe wall. The reaction force is caused by the inertia force of the moving and then quickly ceasing to move striker. The reaction force is used to initiate oscillation in the vessel body without the striker coming in dynamic contact with the vessel wall.

Figure 11:
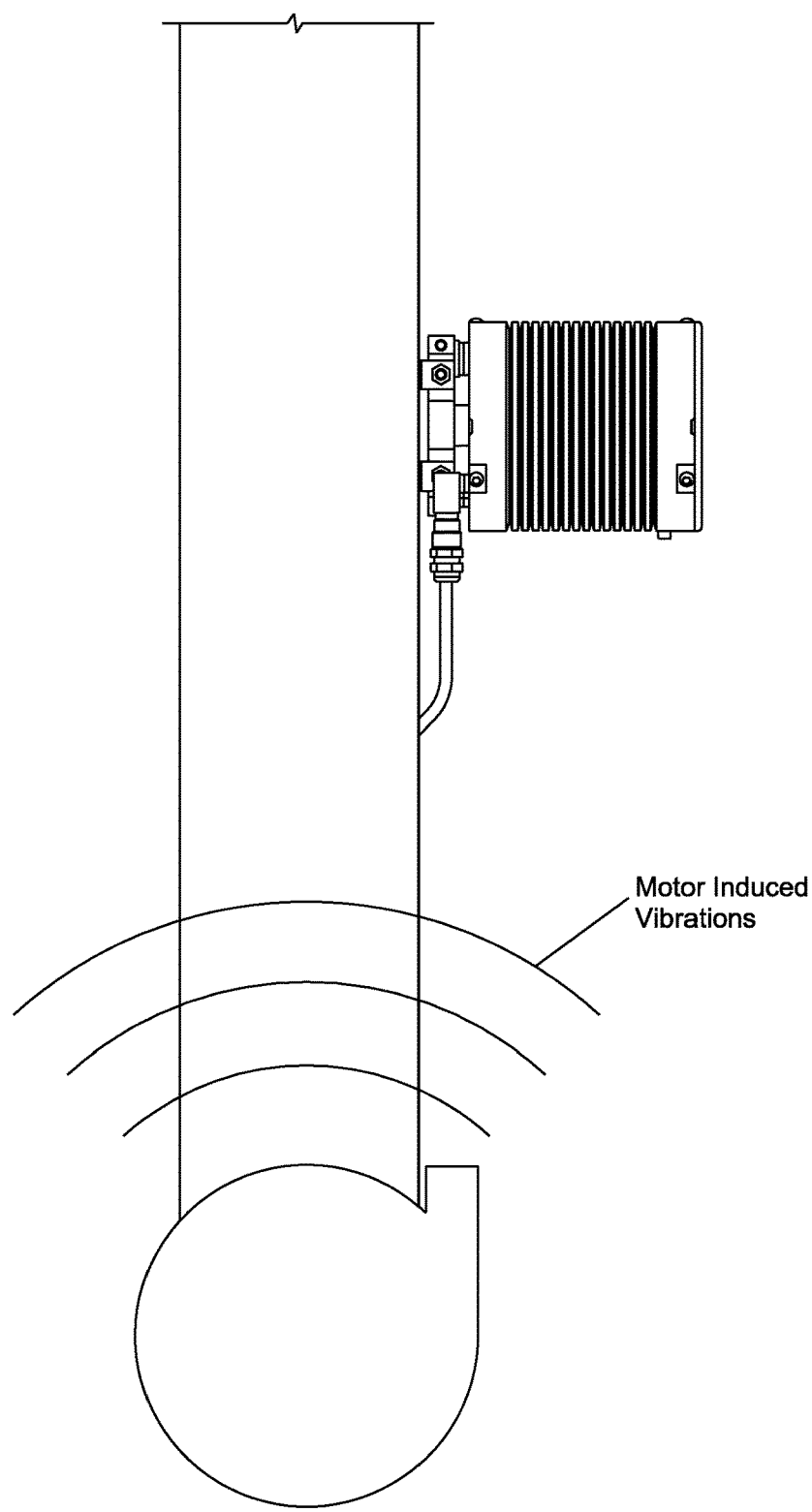
FIG. 11 illustrates actuation via a vibrating member of the vessel's construction.
Figure 12:
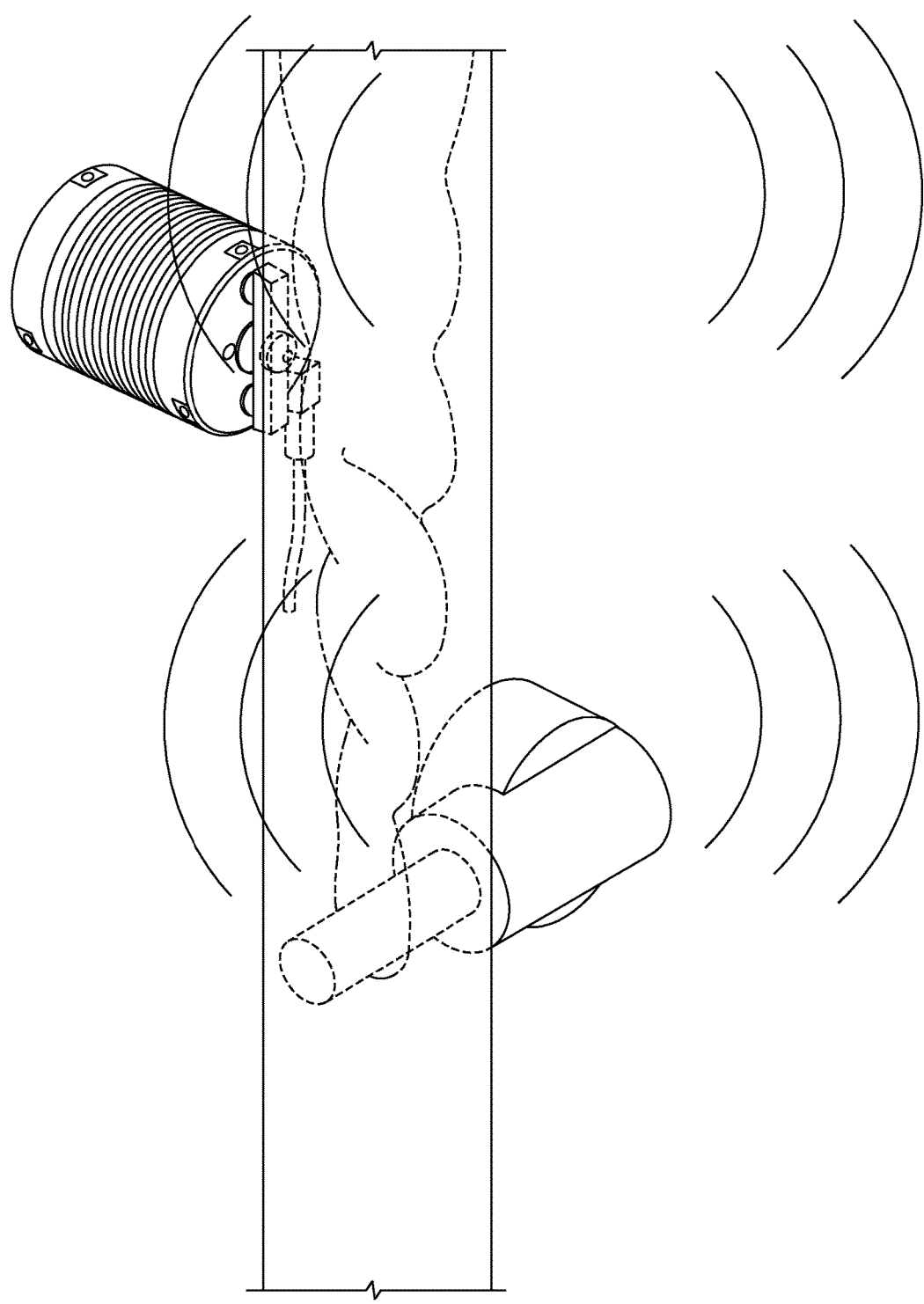
FIG. 12 illustrates actuation caused by a pipe local resistance to moving content material.

In another example illustrated in FIGS. 11 and 12, the vessel body is forced to oscillate by a vibrating member of the vessel's construction such as a motor, a pump, a compactor or a local resistance inside the vessel that causes eddy currents within the material. In this example, the device's sensor acquires the vibration of the vessel body despite the device's striker being immobile.

Figure 13:
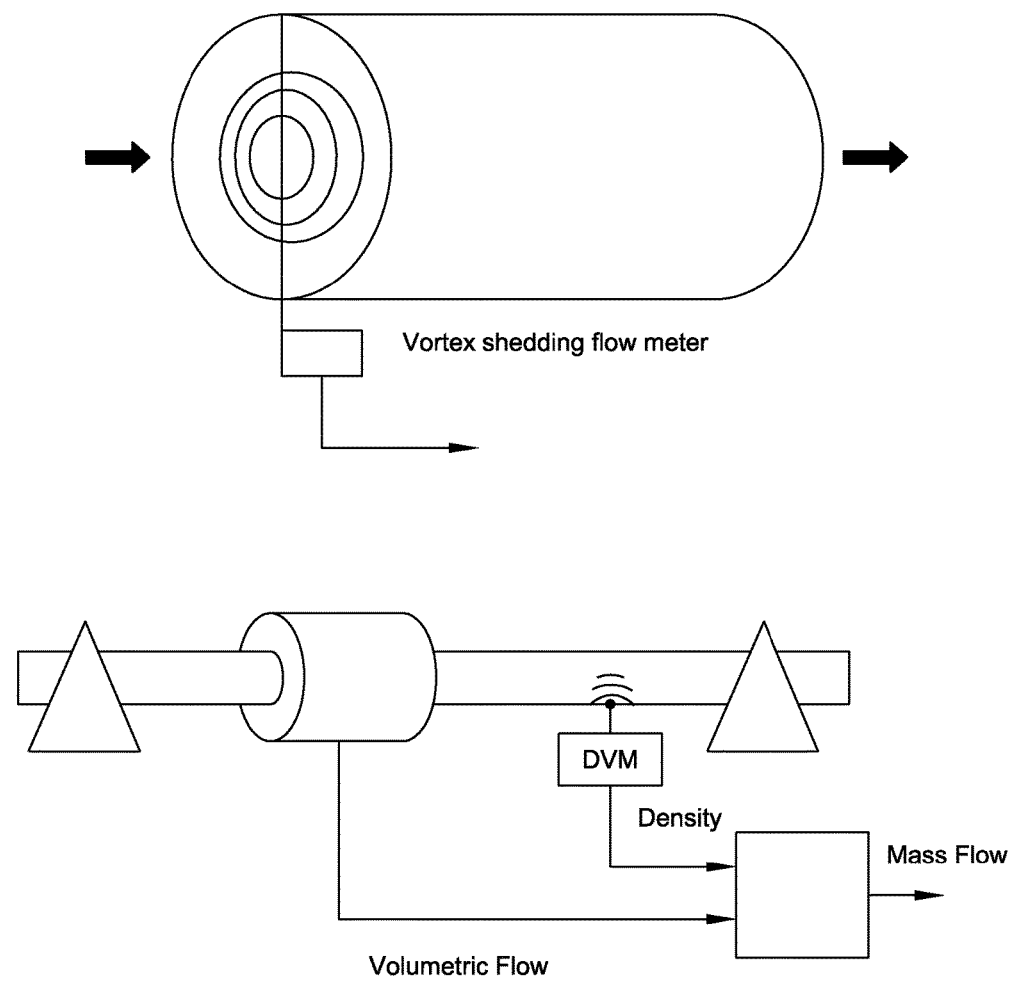
FIG. 13 shows the functional diagram of the device for measuring the mass flow using a combination of the percussion density meter and the volumetric flow meter.

In an application of the device directed to measuring the mass flow rate of the material moving through a pipe, the device is equipped with a volumetric flow measuring unit that measures the mass flow of the pipe content by multiplying the measured material density by the measured volumetric flow. In an example having a vortex-type volumetric flow, the device has an immobile (or removed) striker. This device utilizes pipe body vibration initiated by a source located outside of the device. In particularly, the vibration is initiated by the turbulence generated when the material flow meets resistance from the vortex flow meter shedder member as shown in the functional diagram of FIG. 13.

Figure 14:
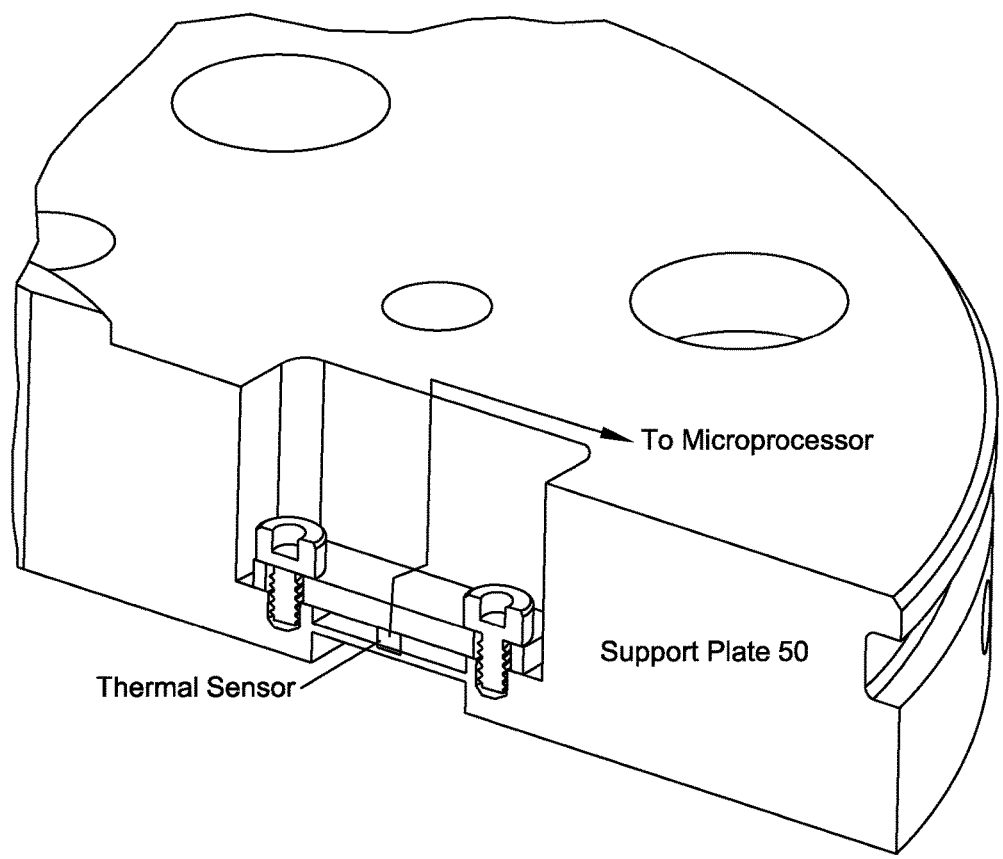
FIG. 14 illustrates positioning of a thermal sensor for monitoring the temperature of the ambient air and calculating the process temperature within the pipe or vessel, thereby providing for the device's invariance to ambient temperature changes and for measuring the content material physical property at a set temperature that differs from the instantaneous process temperature.

In another example, as shown in the FIG. 14, the support plate 50 is modified to accommodate a thermal sensor located in high proximity to the outer wall of the support plate thereby allowing for monitoring ambient air temperature variations. As is described further below, the signal from this thermal sensor is used to create a link to the device's output that provides for the high stability of measurement under wide changes of the ambient air temperature.

In another example, the output from the first temperature sensor located within the support plate 50 is connected to the microprocessor. The output of the second temperature sensor located in proximity to the vibration sensing mechanism is also connected to the microprocessor. The second temperature sensor measures temperature around the vibration sensing means electronics. As is described further below, a simultaneous use of two thermal sensors provides for establishing a highly effective thermal stability link within the device. In addition, the output of the first thermal sensor can be used for calculating the value of the process temperature within the pipe or vessel.

Figure 15:
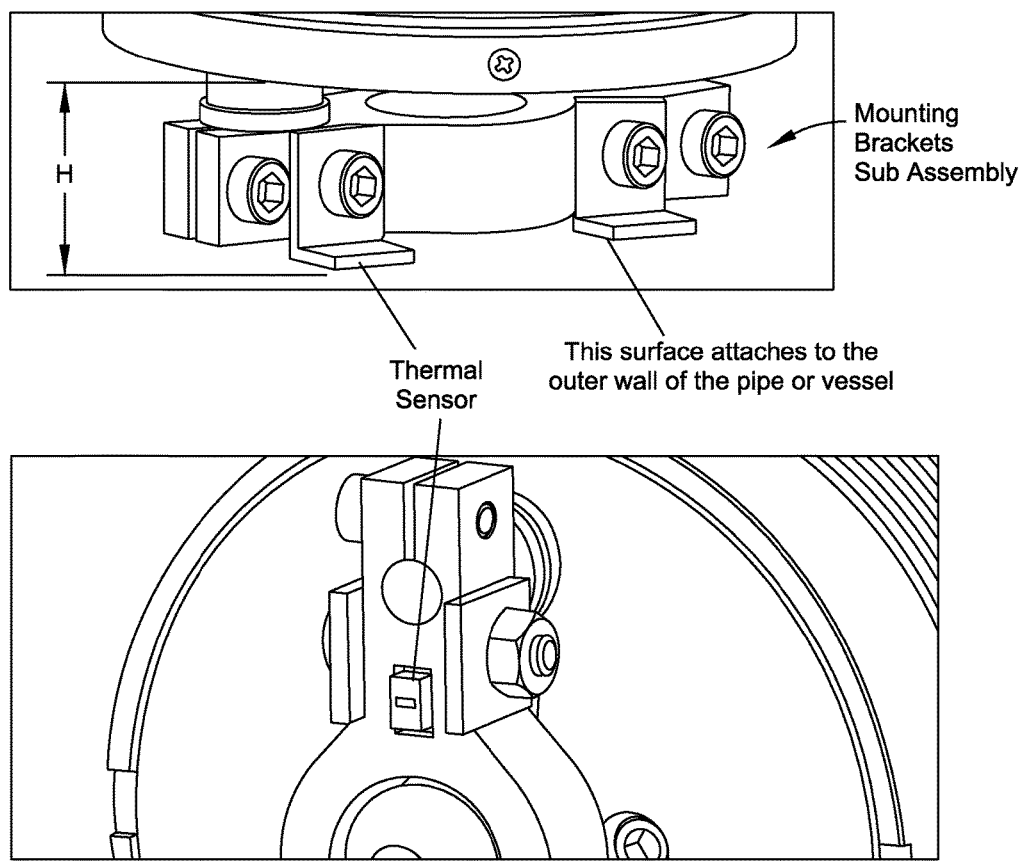
FIG. 15 illustrates positioning of the thermal sensor for the high-accuracy monitoring the process temperature within the pipe or vessel for the purpose of measuring the content material physical property at a set temperature that differs from the instantaneous process temperature.

In another device, as shown in the FIG. 15, at least one thermal sensor is incorporated into the mounting bracket of the device that is used for the device's attachment to the pipe or vessel. This sensor's output is used for an accurate calculation of the process temperature required in those cases when there is a need in measuring the content material physical property at a set temperature that differs from the instantaneous process temperature.

Measurement Processes

Exemplary methods disclosed herein are based on monitoring the oscillatory motion of the segment of the vessel defined by the mechanical members that affix the vessel to a rigid plain that is substantially immobile relative to the vessel. Such motion may be initiated by the application of a temporal mechanical load directed at the wall. Such motion may be initiated by an external source of vibration such as a working pump, a motor, a compactor and similar objects. In this regard, a zero order approximation mechanical system, the properties of which the method exploits, can be classified as the beam with a uniformly distributed mass and a concentrated mass attached to the beam. In this model or approximation, the mass of the empty pipe segment together with the mass of the material constitute the mass of the pipe filled with the material that is used in the approximate beam model of the vessel. The oscillation of the beam is used to obtain information for determining several physical properties of the material filling the pipe segment including the density of this material, among others. The method of measurement is applicable to, at least, both basic types of non-gaseous free flowing vessel contents that are liquid materials, homogeneous and non-homogeneous; and loose solids including powders and other granulated materials. Due to the nature of the beam model the method provides for the measurement of the bulk density of these materials.

Figure 4:
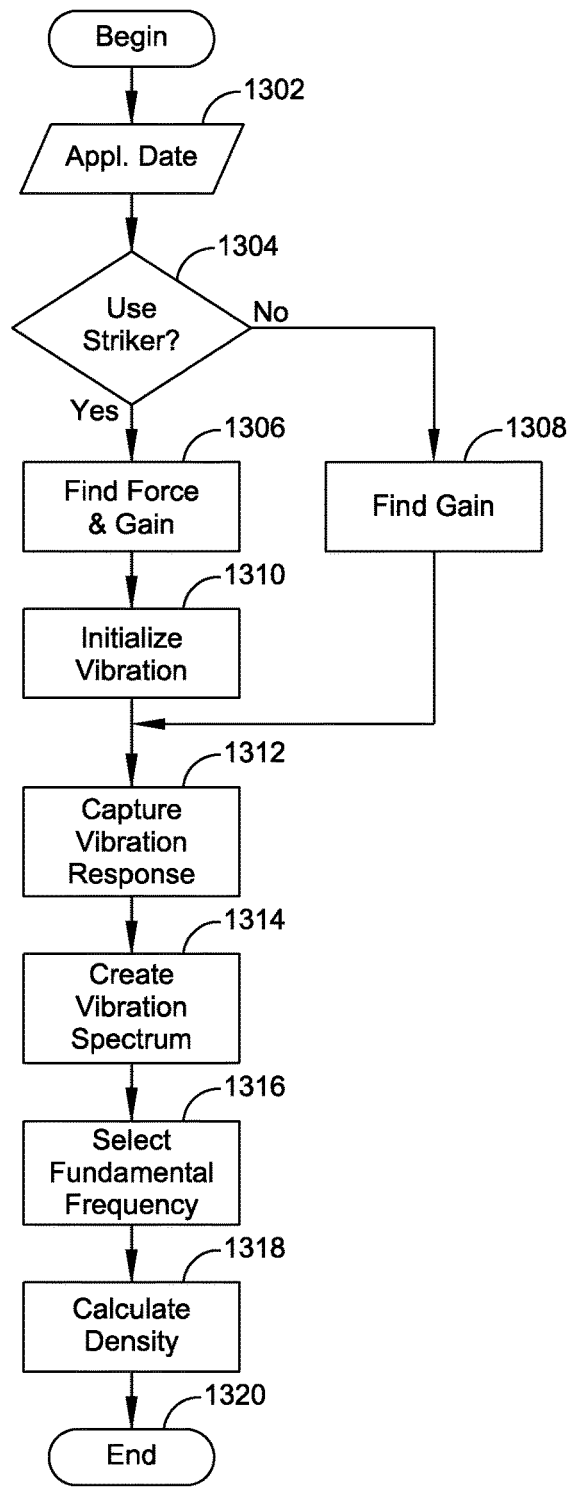
FIG. 4 is a generalized flowchart of the measurement algorithm.
Figure 5:
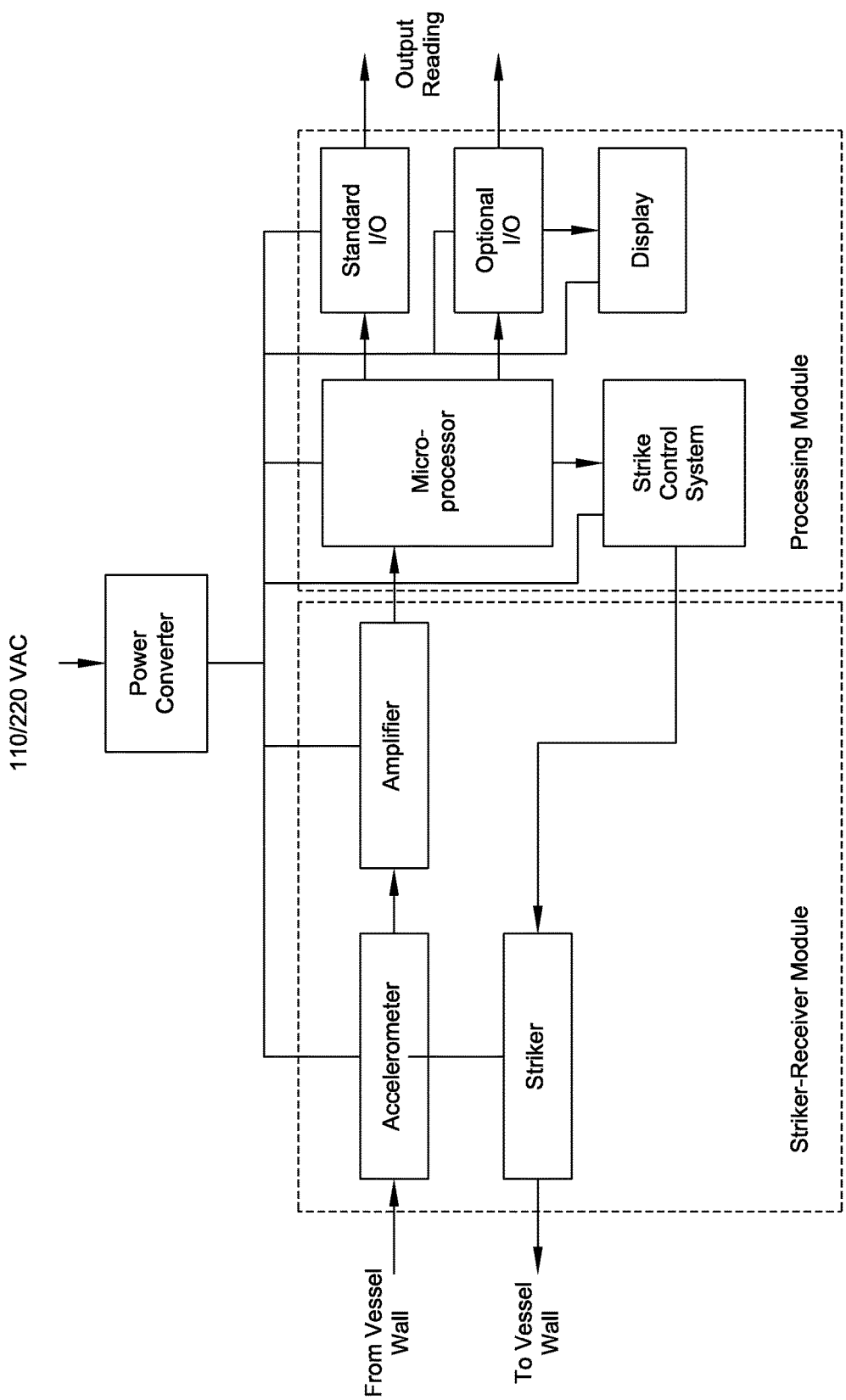
FIG. 5 shows the device's functional block diagram.

Integrally, one example process 1300 is a sequence of the following acts, as illustrated in FIG. 4. The method's flowchart is comprised of two branches that depict two sub methods. A selection of the sub method depends on the manner in which oscillatory motion is imparted to the vessel. Below, the method will be described in its general form including both sub methods. Process 1300 begins at 1302 by the act of entry of data characterizing the vessel and the material filling the vessel. At 1304, the manner in which oscillatory motion is imparted to the vessel is selected. If striking is selected, then at 1306 the measurement apparatus determines acceptable values of the striking force and the vibration sensor gain. If striking is not selected then at 1308 the measurement apparatus determines the acceptable value of the vibration sensor gain. At 1310, the measurement apparatus initiates vibration at least at a single predetermined position on the outside wall of the vessel filled with non-gaseous free flowing matter to the known level. At 1312, the measurement apparatus captures the wall's oscillatory response to the mechanical load. At 1314, the measurement apparatus generates the vibration response signal spectrum (also called a vibration response spectrum). At 1316, the measurement apparatus selects parameters of the vibration spectrum that will be used to generate the measurement. At 1318, the measurement apparatus calculates the values of the measured variables using pre-determined relationships between the selected properties of the vibration spectrum and the measured variables obtained with regards to the measurement application data inserted at 1302. Process 1300 ends at 1320.

Below, each act of the proposed method is described in detail for an example of the method that utilizes a single source of vibration and a single measured variable. In the following method description, for the sake of clarity, the single measured variable will be the density of the material filling the vessel and the vessel type will be a pipe.

Act 1302:

Entering data characterizing the vessel and the material filling the vessel.

The parameters of the vessel and the filling material that are collectively described by the term "Measurement Application Data" should be sufficient for mathematically generating the vibration spectrum in the case of a single degree of freedom dynamic system "beam with a uniformly distributed mass and a concentrated mass attached to the beam." A list of the Measurement Application Data corresponding to this dynamic system is presented below.

1. Pipe outside diameter (OD)
2. Pipe inside diameter (ID) or wall thickness
3. Pipe length between the pipe supports surrounding the measurement apparatus
4. Material of the pipe
5. Expected filling material's mean value of density
6. Type of the pipe supports, e.g., "both ends simply supported" or "both ends clamped"
7. Location of the concentrated mass, e.g., "Mid-span" or "Free end"

Act 1306:

Determining an acceptable value of the striking force that should be applied to a vessel wall for the vessel actuation and an acceptable value of the vibration sensor gain.

The process 1306 executes if striking is selected as the manner in which oscillatory motion is imparted to the vessel. According to the physics of the disclosed method of measuring by percussion, the point level, density or viscosity measurement requires that the sensor output signal satisfy certain conditions of a signal representation. This condition may include a dynamic range value, a time-based window of observation value and a signal decaying behavior. An adaptive strike control process is suggested to support the sensor output signal's satisfaction of the conditions of the signal representation regardless of parameters of the measurement application. The process performs a search for the acceptable value of the striking force and the gain of the vibration sensor and includes execution of the following operations:

Initializing vibration of the vessel by striking at the wall at a certain beginning value of the striking force and a certain beginning value of the vibration sensor gain Capturing the sensor response Evaluating the sensor output signal against the criteria of the signal representation Adjusting the values of the striking force and the vibration sensor gain using the logic of two nested loops; beginning and ending values of the striking force and the gain are pre-determined by the design of the measurement apparatus Issuing a "Failure to obtain acceptable striking force and vibration sensor gain" message in the case when the force and the gain do not produce a sensor output signal that satisfies the conditions of the signal representation described above Using the obtained acceptable values of the striking force and the vibration sensor gain in the measurement beyond the process 1306 when the force and the gain produce a sensor output signal that satisfies the conditions of the signal representation described above Act 1308:

Determining an acceptable value of the vibration sensor gain.

The process 1308 executes if striking is not selected as the manner in which oscillatory motion is imparted to the vessel actuation and passive vibration sensing is selected instead. The process performs a search for the acceptable value of the gain of the vibration sensor and includes execution of the following operations:

Capturing the sensor response

Evaluating the sensor output signal against the criteria of the signal representation Adjusting the value of the vibration sensor gain using the logic of the loop; beginning and ending values of the vibration sensor gain are pre-determined by the design of the measurement apparatus Issuing a "Failure to obtain vibration sensor gain" message in the case when the gain does not produce a sensor output signal that satisfies the conditions of the signal representation described above Using the obtained acceptable values of the vibration sensor gain in the measurement beyond the process 1310 when the gain produces a sensor output signal that satisfies the conditions of the signal representation described above Act 1310:

Initializing vibration at least at a single predetermined position on the outside wall of a vessel filled with some matter to a predetermined level.

The vibration originates in the neighborhood of a mechanical impact with its center located on the outside wall of the vessel. The impact load's time diagram could be of various forms including a single pulse, a trainload of pulses (also called a pulse train), or a continuous periodical load (also called a continuous periodical pulse) as particular examples. Each load-type allows any kind of modulation, for example, Amplitude Modulation, Frequency Modulation, Pulse Modulation, Pulse-Code Modulation, or their combinations. In some examples, the mechanical impact at the wall may originate via an application of any suitable energy source depending on the technical requirements of the particular measurement project. Suitable energy sources may include a solenoid, a spring, a hydraulic and an air pressure-based drives.

Act 1312:

Capturing the wall oscillatory response to the mechanical load.

A mechanical vibration captured by the receiver of the measuring system is quantified and stored in data storage of a computing mechanism executing the method.

Act 1314:

Producing vibration sensor response signal spectrum.

The stored, quantified dataset is an input for a consequent data processing operation performed by a controller that is coupled to the data storage. This data processing operation results in the generation of the signal's harmonic representation through the application of the Fast Fourier Transform Procedure delivering the signal's amplitude spectrum defined on a range of frequencies.

A search zone within vibration spectrum may be defined by calculating values of the fundamental harmonic frequency that are linked to upper and lower boundary values of the measured density within the known density range and with the consequent broadening of the calculated frequency range to account for possible discrepancies between the theoretical parameters of the single degree of freedom mechanical model and the parameters of the actual measurement application, e.g., pipe stiffness.

Act 1316:

Designating certain properties of the vibration spectrum as estimating variables of the measuring system and obtaining instantaneous values of these estimating variables.

The particular properties of the vibration spectrum used as the estimating variables depend on which physical variable is targeted for measurement. For example, for measuring the density of the filling material, the frequency of the fundamental harmonic of the vibration spectrum should be used.

This is so because a single degree of freedom mechanical dynamic system is characterized by the following relationship between the fundamental harmonic frequency and the parameters of the mechanical dynamic system:

$$f \cong \frac{1}{2\pi}\sqrt{\frac{k}{M}} \quad (1)$$

Where k denotes stiffness; M denotes oscillating mass. Assuming that there is no any additional mass attached to the wall, the expression for the total mass of the pipe segment between the supports can be described as follows.

$$M = M_p + M_c \quad (2)$$

In the formula (2) $M_p$ represents the mass of the empty pipe segment; $M_c$ represents the mass of the filling material in the pipe. For a given empty pipe, the mass of the empty pipe is a constant value (attrition not being considered). However, the mass of the pipe content changes in time. For any pipe segment of the length (L) supported according a pipe support standard (e.g., the ASTM standard), the stiffness of the segment is not affected by changes in the environment including the changes of the ambient temperature, which can be a main measurement disturbing factor. Thus it is true that the density of the filling material is proportional to the square value of the period (T) of the fundamental harmonic, $\rho_c \propto T^2$. In the case of the single degree of freedom system model, this relationship is described by the formula:

$$\rho_c = \frac{kT^2 - 4\pi^2 M_p}{4\pi^2 V_c}$$

Where $V_c$ denotes the volume occupied by the filling material in the pipe segment of the length L.

A similar approach can be taken toward more complex systems including the case of the beam with uniformly distributed mass and a concentrated mass of the measuring device attached to the pipe. Depending on the selected measured variable, the relationship between the properties of the vibration spectrum and the measured variable may have different view and different representation, e.g., a formula or a lookup table. Higher harmonics of the vibration spectrum may participate in these relationships too.

Act 1318:

Calculating values of the measured variables using predetermined relationships between the selected properties of the vibration spectrum and the measured variables obtained with regards to the measurement application data entered at 1302.

Continuing the pipe segment example, a conversion of the estimating variable f into the measured variable $\rho_c$ can be performed using the following formulas.

$$\rho_c = \frac{\beta^4 E I g}{\pi^3 L^4 d^2 f^2} - \frac{4cgM_s}{\pi L d^2} - \frac{\rho(D^2 - d^2)}{d^2} \quad (3)$$

$$I = q(D^4 - d^4)$$

$$M_s = \frac{1}{g}W_s$$

Where D—Pipe OD;
d—Pipe ID;
ρ—Density of the pipe wall material
E—Young Modulus of the pipe wall material I—Moment of Inertia of the pipe cross sectional area
g—Gravity constant
$W_s$—Weight of the vibration sensor used for producing the vibration spectrum
$M_s$—Mass of the vibration sensor
B, c—Measurement application-dependent parameters
q—Measurement units conversion factor It is to be appreciated that another important feature of the examples disclosed herein is that using an adequate mathematical model of the dynamic system "Vessel with Filling Material—Actuator" allows control of the accuracy of measurement by managing the amount of the measurement application data required for the measuring device setup. In the filling material density measurement example described below, the method is modified by the inclusion of acts for controlling the accuracy of the measuring device during the device's installation and setup. In this example the process continues beyond the act 1318.

Act 1320:

Obtaining at least two different values of the measured variable from two different material samples via a standard measuring device or a standard method.

The two values of the measured variable must differ sufficiently to allow an effective improvement of the accuracy of the method. In the particular case of the material density measurement flowing through a 3 in. size pipe of the length 60 in., the difference between the material samples measurement should be greater or equal to 5%.

Act 1322:

Calculating corrected values of the parameters B and c in the formula using the following expressions.

$$B = L\sqrt[4]{\frac{\pi^3 d^2 f_1^2 f_2^2 (\rho_{c2} - \rho_{c1})}{E I g (f_1^2 - f_2^2)}} \quad (4)$$

$$c = \pi L \frac{f_2^2[d^2\rho_{c2} + \rho(D^2 - d^2)] - f_1^2[d^2\rho_{c1} + \rho(D^2 - d^2)]}{4gM_s(f_1^2 - f_2^2)}$$

$$f_j \equiv f_j(t, t^*)$$

$$\rho_{cj} \equiv \rho_{cj}(t, t^*)$$

$$j = 1, 2$$

Where $f_j \equiv f_j(t, t^*)$, j=1, 2 denotes the measuring device-generated frequency of the fundamental harmonic obtained at the moment of time t=t*. $\rho_{cj} \equiv \rho_{cj}(t,t^*)$, j=1, 2 denotes the density of the material sample obtained at the same moment of time t=t*.

Act 1324:

Substituting values of the parameters B and c in the formula (3) with their values calculated using the formula (4).

Act 1326:

Calculating corrected values of the filling material density using the formula (3).

Act 1328:

Obtaining at least one value of the measured variable from a material sample via a standard measuring device or a standard method.

The material sample measurement could be a single measurement or a statistically processed measurement (e.g., averaged by a number of measurements on the same material sample).

Act 1328:

Calculating the measured variable's offset value as follows.

$$\Delta\rho = \rho_c^*(t=t^*) - \rho_c^0(f,t=t^*) \qquad (5)$$

Where $\rho_c^*(t=t^*)$ denotes the material sample density measurement by the standard device or the standard method; the measurement time-stamped at $t=t^*$; $\rho_c^0(f,t=t^*)$ denotes the measurement of the filling material density produced by the measuring instrument of the method disclosed herein using the formula (3) and time-stamped at $t=t^*$.

Act 1330:

Calculating the corrected value of the measured variable using the following formula.

$$\rho_c = \rho_c^0 + \Delta\rho \qquad (6)$$

The theory behind the formula (6) is that the density described by the formula (3) is represented by a family of almost parallel curves thereby making the correction (6) useful. The process 1300 of this example of the method ends at 1332.

Depending on the measurement application's specification, certain acts can be skipped in the example of the method described above. For example, in the case where trend analysis is required, the acts 1320-1332 from the second method example may be skipped and the outcome of the measuring device will be governed by the acts 1302-1320 of the first example of the measurement method. In the case when the accuracy of the measuring device should be sufficient for a typical process control application, the acts 1320-1326 may be skipped in the second example of the measurement method. The entire method of the second example should be used for obtaining the best accuracy of measurement.

In another example, to further enhance the long term stability of the measurement method, the method includes computation of a correction to the measured variable values to account for noise caused due the susceptibility to thermal energy of electronic parts of a vibration sensor. In this example, the correction is computed as a function of a link between the temperature inside the vibration sensor and the measured variable. In another example, the method includes computation of another correction to the measured variable values to account for noise caused due the susceptibility to thermal energy of mechanical parts of the vibration sensor. In this example, the correction is computed as a function of a link between the ambient temperature and the measured variable. The utilization of the links depends on the environmental conditions such that each of the links could be used solely and independently or both links could be used simultaneously and in some interrelationship.

In another example of the method, the ambient temperature data obtained within a predefined proximity of the vessel's outer surface could be used for implementing the process temperature compensation function when certain properties should be measured at a set process temperature regardless of the temperature value existing on the moment of measurement. When executed, this temperature compensation function converts a value of physical property measured at a recorded temperature to a value (i.e., a compensated value) that the physical property would be measured to have at the set process temperature. This function is important in various chemical engineering measurement applications.

The various temperature-based corrections and compensations described herein are additional acts executed within some examples of the earlier described measurement process 1300 that modify the generated output readings in accordance with the acts of the process 1300.

Process 1300 depicts one particular sequence of acts in a particular example. The acts included in process 1300 may be performed by, or using, one or more computer systems specially configured as discussed herein. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely a measurement device configured according to the examples disclosed herein.

Having thus described several aspects of at least one embodiment, it is to be appreciated various alterations, modifications, and improvements will readily occur to those skilled in the art. Such alterations, modifications, and improvements are intended to be part of this disclosure, and are intended to be within the scope of the embodiments discussed herein. Accordingly, the foregoing description and drawings are by way of example only.

What is claimed is:

1. A method for measuring physical properties of non-gaseous free flowing material in a vessel, the method comprising:
   receiving data characterizing the vessel and at least one sample of the material in the vessel;
   initiating a vibration on a wall of the vessel by one of an external source or an internal source in mechanical communication with the vessel;
   capturing a response to the vibration;
   generating a vibration response spectrum based on the response;
   determining a search zone within the vibration response spectrum based on a configuration of the vessel, a type of attachment between the vessel and another object, and the at least one sample of the material in the vessel;
   determining at least one pre-established relationship between at least one physical property of the material and one or more characteristics of the vibration response spectrum of the search zone;
   measuring an ambient temperature within a predefined proximity of the vessel;
   determining a difference between the measured ambient temperature and a set process temperature;
   computing a correction to the at least one pre-established relationship based on the difference; and
   calculating at least one value of at least one physical property of the material based on the at least one corrected pre-established relationship.

2. The method of claim 1, wherein initiating the vibration includes at least one of initiating a solid body interaction with the wall, initiating a fluid-dynamic interaction with the wall, initiating a ballistic percussion interaction with the wall, or initiating an electro-dynamic interaction with the wall.

3. The method of claim 1, wherein initiating the vibration includes applying a mechanical load to the outside wall of the vessel, and the mechanical load includes at least one of a single pulse, a pulse train, or a periodic pulse.

4. The method of claim 3, wherein the mechanical load is modulated according to at least one of amplitude modulation, frequency modulation, pulse modulation, pulse-code modulation, or pulse-width modulation.

5. The method of claim 1, wherein capturing the response includes:
   converting an oscillation into a digital signal;
   analyzing the digital signal to calculate one of a wall response time, a damping factor, a signal harmonic spectrum, or a variable characterizing a magnitude of the oscillation; and
   adjusting a gain applied to the response.

6. The method of claim 1, wherein calculating the at least one value includes calculating at least one value of material level in the vessel, material bulk density, kinematic viscosity, or dynamic viscosity of the material.

7. The method of claim 1, wherein calculating the at least one value includes calculating at least one value of at least one physical property of a homogeneous liquid, a heterogeneous liquid, or a loose solid.

8. The method of claim 1, wherein calculating the at least one value includes calculating at least one value of at least one physical property of a moving material or a still material.

9. The method of claim 1, wherein the vessel is one of a silo, a tank, or a pipe.

10. The method of claim 1, wherein calculating the one or more characteristics of the vibration response spectrum of the search zone is a frequency of one of a spectrum harmonic.

* * * * *